United States Patent [19]
Konik et al.

[11] Patent Number: 6,060,072
[45] Date of Patent: *May 9, 2000

[54] TRANSFER RESISTANT COLOR COSMETIC COMPOSITIONS

[75] Inventors: Richard A. Konik, Sayville; Rachel J. Painter, E. Setauket; George J. Stepniewski, Melville; Suzanne J. Davis, Balldwin, all of N.Y.

[73] Assignee: Color Access, Inc., Melville, N.Y.

[ * ] Notice: This patent is subject to a terminal disclaimer.

[21] Appl. No.: 08/985,770

[22] Filed: Dec. 5, 1997

Related U.S. Application Data

[63] Continuation-in-part of application No. 08/962,100, Oct. 31, 1997, Pat. No. 5,959,009.

[51] Int. Cl.[7] .................................................. A61K 7/00
[52] U.S. Cl. ...................... 424/401; 424/70.7; 424/70.11; 424/70.12; 424/70.15; 424/78.02; 424/78.18
[58] Field of Search .................................. 424/401, 70.7, 424/70.11, 70.12, 70.15, 78.18, 78.02

[56] References Cited

U.S. PATENT DOCUMENTS

| | | | |
|---|---|---|---|
| 5,026,540 | 6/1991 | Dixon et al. | 424/60 |
| 5,221,534 | 6/1993 | DesLauriers et al. | 424/78.03 |
| 5,356,627 | 10/1994 | Da Cunha et al. | 424/401 |
| 5,389,363 | 2/1995 | Snyder et al. | 424/70.7 |
| 5,756,082 | 5/1998 | Cashin et al. | 424/78.03 |

FOREIGN PATENT DOCUMENTS

| | | |
|---|---|---|
| 497144 B1 | 5/1992 | European Pat. Off. . |
| 09143029 | 6/1997 | Japan . |
| WO 92/19215 | 12/1992 | WIPO . |
| WO 94/12190 | 6/1994 | WIPO . |
| WO 94/17775 | 8/1994 | WIPO . |
| WO 97/29842 | 12/1997 | WIPO . |
| WO 98/42298 | 10/1998 | WIPO . |

*Primary Examiner*—Thurman K. Page
*Assistant Examiner*—Lakshmi Channavajjala
*Attorney, Agent, or Firm*—Dorene M. Price, Esq.; Karen A. Lowney, Esq.

[57] ABSTRACT

The invention relates to transfer-resistant color cosmetic compositions comprising a film forming agent, a volatile oil, a styrene-ethylene-propylene copolymer as gellant, and optionally, a pigment.

7 Claims, No Drawings

TRANSFER RESISTANT COLOR COSMETIC COMPOSITIONS

RELATED APPLICATIONS

This application is a continuation-in-part of U.S. Ser. No. 08/962,100, filed Oct. 31, 1997, now U.S. Pat. No. 5,959,009, the contents of which are incorporated herein by reference in their entirety.

FIELD OF THE INVENTION

The invention relates to cosmetic compositions. More specifically, the invention relates to waterproof and transfer-resistant cosmetic compositions.

BACKGROUND OF THE INVENTION

There is currently a very strong trend among cosmetics consumers to want products that last the day without the need for refreshing or touching up. It is preferred that a color cosmetic product applies easily, leaving a clear vivid color which remains in place at least through the work day, and preferably into the evening. Given the hectic lifestyles of most consumers, however, providing such a product is not a simple task. Daily physical activity, particularly in the form of daily exercise, which is now so common, is not conducive to makeup retention, with the combination of perspiration and body oils routinely washing away the typical color products with very little effort. In addition, it is also preferred that the product not readily transfer from the place of application. Consumers no longer readily accept a lipstick which leaves its color on a coffee cup, or a foundation which leaves smudges on the collar of a white blouse. Although many currently available products attempt to achieve this desired long-lasting property, there are often other undesirable properties, such as dryness, or difficulty in application, that go along with ability to remain in place on the skin. Thus, there continues to be a need for a color cosmetic which applies smoothly, which is not subject to smearing, flaking, or smudging, and also retains a strong, non-fading color throughout the day. The present invention now provides such a product.

SUMMARY OF THE INVENTION

The present invention relates to a water-proof or water resistant cosmetic composition for application to the skin comprising a volatile oil solvent, a film-forming agent, and a styrene-ethylene-propylene copolymer as gellant. In a preferred embodiment, the composition also contains a pigment. The unpigmented composition can be used for waterproofing non-waterproof color cosmetics, such as a non-waterproof eyeliner. When pigment-containing, the compositions of the invention can be any type of color cosmetic, for example, foundations, blushes, lipsticks or glosses, mascaras for hair and lashes, eyeshadows and eyeliners. The compositions of the invention are waterproof, smudgeproof, non-flaking and when pigmented, transfer-resistant, retaining vibrant color on the skin, with substantially no transfer or fading, for several hours up to a full day.

DETAILED DESCRIPTION OF THE INVENTION

The compositions of the invention have a volatile oil base, which provides for a very quick-drying product, which in turn reduces the tendency to smear. Suitable volatile oils for use in the composition include, but are not limited to, both cyclic and linear silicones, such as hexamethylcyclotrisiloxane, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins. Preferred volatile oils are a C8–9 isoparaffin, such as is commercially available from Exxon Corporation, as Isopar E®, or a $C_9$–$C_{12}$ aliphatic hydrocarbon, such as is commercially available under the tradename Permethyl® 99A, from Permethyl Corp., Frazer, Pa.), or a combination of these. The volatile oil component constitutes from about 1–90%, preferably about 50–85%, by weight of the total composition.

Combined with the volatile oil is at least one film-forming agent, which provides a waterproofing property to the composition, improving the wear of the composition, and also conferring transfer-resistance to the makeup product. The film-forming agent may be any which is cosmetically acceptable. Examples of useful film-forming agents include natural waxes, polymers such as polyethylene polymers, and copolymers of PVP, ethylene vinyl acetate, dimethicone gum, and resins, such as shellac, polyterpenes, and various silicone resins, e.g., trimethylsiloxysilicate. The film-former is used in an amount of from about 0.1–50%, more preferably from about 1–20%. Particularly preferred film-formers are PVP copolymers, such as PVP/eicosane copolymer or a tricontanyl PVP, which produce a smooth, non-tacky film on the skin. Such copolymers are commercially available under the tradename Ganex® from GAF.

In order to incorporate pigment into the volatile oil-film-former combination, it is necessary to add a gellant; in the absence of a gellant, the pigment will simply fall out of suspension. In this type of formula, the most commonly used gellants are clay-based gellants, such as bentone, which when used as the sole gellant, may not always produce a clear gel. Moreover, the use of clay-based gellants like bentone as the sole gellant, depending on the film-forming agent employed, can result in a product which is unstable, allowing leakage of solvents and emollients from the gel matrix. To avoid these problems, a styrene-ethylene-polypropylene copolymer is used as gellant. The use of a styrene-ethylene-polypropylene copolymer as gellant results in a very translucent, non-cloudy, shiny product which permits the true color of the pigment to come through. The pigment readily remains in suspension, and the product so prepared also retains stability over prolonged periods of time, thereby producing a superior product to one in which a clay-based solvent is used. In addition, even in the absence of a pigment, a desirable viscosity enhancement is achieved by the use of the copolymer.

The copolymer gellants of the invention are particulate diblock copolymers having the formula S-EP, wherein "S" denotes a block comprising styrene monomers and "EP" denotes a block comprising ethylene and propylene monomers. These materials are well known in the art, and are available commercially, for example, from Shell Chemical Company, Oak Brook, Ill. under the tradename "Kraton® G rubber". A particularly preferred material is Kraton® G-1701X. The amount of the gellant used in the formulation is from about 1–15%, more preferably 3–8% by weight of the total composition.

In a preferred embodiment, the composition contains less than 5%, and preferably none, of a non-volatile oil component. The use of a non-volatile oil can cause plasticizing of the film-forming agent, thereby reducing the product's resistance to smudging. The absence of a non-volatile oil thus results in a product with greater wear. With the use of a pliable film-former such as Ganex®, a non-volatile oil is unnecessary to soften it; however, if a harder, or more brittle, film-former is used, a small amount of non-volatile oil may be necessary to achieve the desired consistency of the product.

Additional preferred components of the cosmetic compositions of the invention include one or more pigments. Any cosmetically acceptable pigment, either organic, inorganic, or combinations thereof, can be used in the makeup compositions of the invention. Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof.

It will be recognized that when the product is, for example, an eyeliner or other eye product, the pigment should be one the use of which is approved for the eye area. Examples of useful pigments for the eye are metallic oxides, such as titanium or iron oxides, bismuth oxychloride, carmine, chromium oxide or chromium hydroxide greens, ultramarines, ferric ferrocyanide, ferric ammonium ferrocyanide, mica, FD&C blue No. 1, FD&C Red No.40, FD&C yellow No. 5, and FD&C green No. 5. Pigment concentrations will vary depending upon the color of the final product, but generally will be in the range of from about 0.1 to about 30% more preferably from about 1 to about 20%, by weight of the total composition.

The compositions of the invention may also comprise additional, optional components. For example, it may be desirable to add one or more preservatives or antioxidants to the formulation. Appropriate preservatives may include propyl paraben, butyl paraben, mixtures thereof, or isoforms thereof, as well as BHA or BHT.

In particularly preferred embodiments, the compositions of the invention are used as a liquid eyeliner, or as a body paint. In the latter embodiment, the composition can be used to create long-lasting, yet temporary, tattoos or designs on the skin.

The invention is further illustrated by the following non-limiting examples:

EXAMPLES

Example I

A formulation according to the invention is prepared as follows:

| Material | Weight % |
| --- | --- |
| Phase 1 | |
| C8-9 isoparaffin | 64.85 |
| Phase 2 | |
| styrene-ethylene-propylene copolymer | 5.00 |
| trimethylsiloxysilicate | 5.00 |
| PVP/eicosene copolymer | 5.00 |
| tricontanyl PVP | 5.00 |
| polyethylene | 5.00 |
| isododecane/quaternium-18 hectorite | 0.10 |
| BHT | 0.10 |
| Phase 3 | |
| iron oxides/methicone | 10.00 |

The Phase 2 components are dissolved in Phase 1 component at about 90° C., and mixed to homogeneity. Phase 3 components are then added to the mixture until homogeneously dispersed.

The product so prepared is stable, waterproof, and highly resistant to smudging.

What we claim is:

1. A waterproof or water resistant cosmetic composition which comprises a styrene-ethylene-propylene copolymer in an amount of from about 5 to about 10%, a combination of a PVP/eicosene copolymer and a tricontanyl PVP copolymer in an amount of from about 0.1% to about 50%, a C8–9 isoparaffin, a $C_9$–$C_{12}$ aliphatic hydrocarbon, or a combination thereof, in an amount of from about 50 to about 85%.

2. The composition of claim 1 which further comprises a pigment in an amount of from about 1 to about 30%.

3. A waterproof or water resistant cosmetic composition which comprises a styrene-ethylene-propylene copolymer in an amount of from about 5 to about 10%, a combination of a PVP/eicosene copolymer and a tricontanyl PVP copolymer in an amount of from about 0.1% to about 50%, a C8–9 isoparaffin, a $C_9$–$C_{12}$ aliphatic hydrocarbon, or a combination thereof, in an amount of from about 50 to about 85%, and a metallic oxide pigment in an amount of from about 1 to about 30%.

4. The composition of claim 1 which further comprises at least one other film-forming agent, in an amount of from about 1–10%.

5. The composition of claim 3 which further comprises at least one other film-forming agent, in an amount of from about 1–10%.

6. The composition of claim 4 wherein at least one other film-forming agent is selected from the group consisting of polyethylene and trimethylsiloxysilicate.

7. The composition of claim 5 wherein at least one other film-forming agent is selected from the group consisting of polyethylene an trimethylsiloxysilicate.

* * * * *